(12) United States Patent
Takeuchi

(10) Patent No.: US 10,688,225 B2
(45) Date of Patent: Jun. 23, 2020

(54) SUCTION DEVICE

(71) Applicant: MURATA MANUFACTURING CO., LTD., Kyoto (JP)

(72) Inventor: Susumu Takeuchi, Kyoto (JP)

(73) Assignee: MURATA MANUFACTURING CO., LTD., Kyoto (JP)

( * ) Notice: Subject to any disclaimer, the term of this patent is extended or adjusted under 35 U.S.C. 154(b) by 704 days.

(21) Appl. No.: 15/337,027

(22) Filed: Oct. 28, 2016

(65) Prior Publication Data
US 2017/0043065 A1    Feb. 16, 2017

Related U.S. Application Data

(63) Continuation of application No. PCT/JP2015/059307, filed on Mar. 26, 2015.

(30) Foreign Application Priority Data

Apr. 30, 2014    (JP) .................... 2014-094271

(51) Int. Cl.
*A61M 1/00*    (2006.01)
*F04B 45/047*    (2006.01)

(52) U.S. Cl.
CPC ........ *A61M 1/0003* (2013.01); *A61M 1/0066* (2013.01); *A61M 1/0072* (2014.02);
(Continued)

(58) Field of Classification Search
CPC .............. A61M 1/0003; A61M 1/0072; A61M 1/0066; A61M 1/0618; A61M 2205/8206; F04B 45/047; F04B 43/046
(Continued)

(56) References Cited

U.S. PATENT DOCUMENTS 5,205,819 A * 4/1993 Ross ................ A61M 5/14224
128/DIG. 12
6,471,679 B1 * 10/2002 Suh ..................... A61M 1/0023
604/319
(Continued)

FOREIGN PATENT DOCUMENTS

JP    H04-51956 U    5/1992
JP    20000325466 A    11/2000
(Continued)

OTHER PUBLICATIONS

International Search Report Issued in Application No. PCT/JP2015/059307 dated Jun. 23, 2015.
(Continued)

*Primary Examiner* — Charles G Freay
(74) *Attorney, Agent, or Firm* — Pearne & Gordon LLP

(57) ABSTRACT

A suction device (1) having a suction port (90) exposed outside, a flow passage (91 to 98) communicating with the suction port (90), and a discharge port (99) through which fluid is discharged from the flow passage (91 to 98) includes a diaphragm (83) having one principal surface facing a pump chamber (98) and the other principal surface opposed to the one principal surface, and a piezoelectric element (81) attached to the diaphragm (83) to displace the one principal surface of the diaphragm (83) relative to the pump chamber (98). The one principal surface and the other principal surface of the diaphragm (83) face in a direction different from a direction to which the suction port (90) faces.

20 Claims, 4 Drawing Sheets

(52) U.S. Cl.
CPC ... *F04B 45/047* (2013.01); *A61M 2205/8206* (2013.01); *A61M 2210/0618* (2013.01)

(58) Field of Classification Search
USPC .......................................... 417/413.2, 413.3
See application file for complete search history.

(56) References Cited

U.S. PATENT DOCUMENTS

| | | | | |
|---|---|---|---|---|
| 6,595,949 | B1* | 7/2003 | Shapiro | A61M 1/0023 604/315 |
| 6,869,275 | B2* | 3/2005 | Dante | F04B 43/046 251/129.06 |
| 7,600,987 | B2* | 10/2009 | Seto | F04B 17/003 417/413.1 |
| 10,107,281 | B2* | 10/2018 | Tanaka | F04B 45/047 |
| 2004/0021398 | A1* | 2/2004 | East | F04B 43/04 310/311 |
| 2009/0076441 | A1* | 3/2009 | Sebban | A61M 1/0003 604/35 |
| 2009/0167109 | A1* | 7/2009 | Tomita | F04B 43/046 310/317 |
| 2012/0286626 | A1 | 11/2012 | Matsuo | |
| 2013/0304007 | A1* | 11/2013 | Toth | A61M 1/0031 604/321 |
| 2014/0178227 | A1* | 6/2014 | Richter | F04B 39/10 417/470 |
| 2015/0157773 | A1 | 6/2015 | Baker et al. | |

FOREIGN PATENT DOCUMENTS

| | | |
|---|---|---|
| JP | 2004517240 A | 6/2004 |
| JP | 2009264135 A | 11/2009 |
| JP | 2010527636 A | 8/2010 |
| JP | 2014504190 A | 2/2014 |
| WO | 2011078218 A1 | 6/2011 |
| WO | 2011090201 A1 | 7/2011 |

OTHER PUBLICATIONS

Written Opinion Issued in Application No. PCT/JP2015/059307 dated Jun. 23, 2015.

* cited by examiner

THICKNESS DIRECTION

LONGITUDINAL DIRECTION

WIDTH DIRECTION

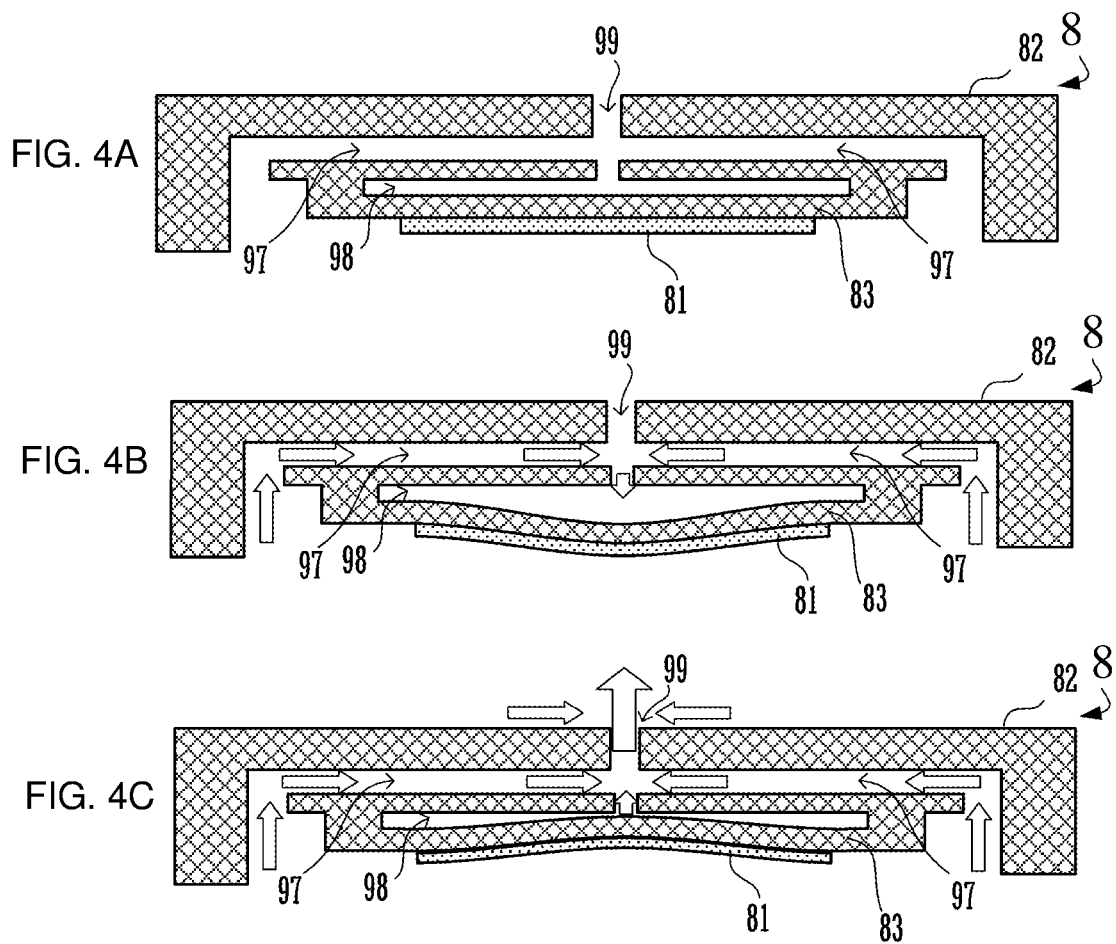
FIG. 4A
FIG. 4B
FIG. 4C
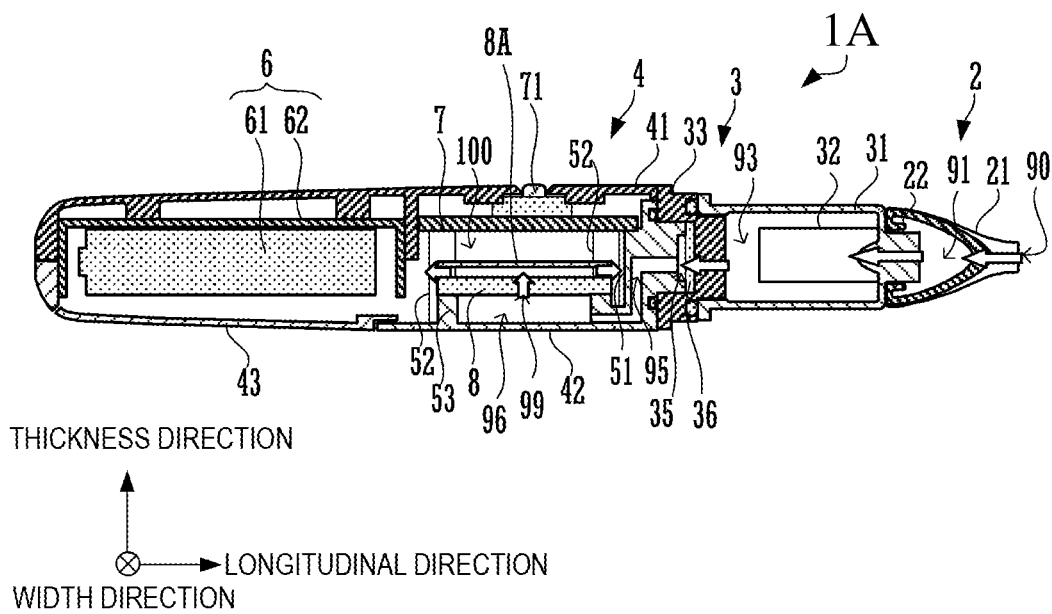
FIG. 5

SUCTION DEVICE

This is a continuation of International Application No. PCT/JP2015/059307 filed on Mar. 26, 2015 which claims priority from Japanese Patent Application No. 2014-094271 filed on Apr. 30, 2014. The contents of these applications are incorporated herein by reference in their entireties.

BACKGROUND OF THE DISCLOSURE

Field of the Disclosure

The present disclosure relates to a suction device used to remove, for example, liquid such as nasal mucus.

Description of the Related Art

For example, cold, nasal inflammation, and empyema cause a symptom, such as nasal congestion, due to excessive secretion of nasal mucus. Although nasal congestion is generally relieved by nose blowing, for example, nasal mucus of infants who cannot blow their noses needs to be removed by a helper. At this time, a little nasal mucus can be removed with a tissue or a cotton swab, but it is difficult to remove a lot of nasal mucus. Accordingly, suction devices capable of removing a lot of nasal mucus by using an electric motor and a pump have recently been spread (see, for example, Patent Document 1).

Patent Document 1: Japanese Unexamined Patent Application Publication (Translation of PCT Application) No. 2010-527636

BRIEF SUMMARY OF THE DISCLOSURE

However, in the conventional suction devices, motor sound and vibration caused during use are large, an infant or the like moves his or her body in response to the motor sound and vibration, and this sometimes makes it difficult to perform the operation of sucking nasal mucus. Accordingly, the present applicant has developed a suction device in which a piezoelectric element that causes little motor sound and vibration during use is used instead of the electric motor.

FIG. 6 schematically illustrates a suction device using a piezoelectric element as a driving source. A suction device 101 includes a nozzle 102, a separator 103, and a piezoelectric driving unit 104. The nozzle 102 is inserted in a nasal cavity or the like to suck external fluid. The separator 103 is connected to a rear end of the nozzle 102, and separates nasal mucus sucked by the nozzle 102 from air. The piezoelectric driving unit 104 is connected to a rear end of the separator 103, sucks the air separated by the separator 103, and discharges the air to the outside. The piezoelectric driving unit 104 includes a diaphragm 105 and a piezoelectric element 106. The diaphragm 105 is provided to be opposed to a discharge port. The piezoelectric element 106 is driven to vibrate the diaphragm 105. In the suction device 101 having such a structure, driving of the piezoelectric element 106 is not accompanied by sliding and friction, and this can greatly reduce the driving sound and vibration.

In the piezoelectric element, however, high-frequency audible sound that is not produced by the electric motor, that is, so-called mosquito sound is sometimes produced by vibration. This high-frequency audible sound sometimes causes a rejection reaction of infants and the like.

Accordingly, an object of the present disclosure is to provide a suction device that can suppress the influence of high-frequency audible sound.

A suction device according to the invention disclosure having a suction port exposed outside, a flow passage communicating with the suction port, and a discharge port through which fluid is discharged from the flow passage includes a vibrating plate having one principal surface facing the flow passage and the other principal surface opposed to the one principal surface, and a piezoelectric element attached to the vibrating plate to displace the one principal surface of the vibrating plate relative to the flow passage. The one principal surface and the other principal surface of the vibrating plate face in a direction different from a direction to which the suction port faces (a direction in which liquid or the like is sucked from the suction port).

In this suction device, driving of the piezoelectric element is not accompanied by sliding and friction, and this can greatly reduce the driving sound and vibration. Moreover, even when high-frequency audible sound is caused by vibration of the piezoelectric element, the orientation direction of the high-frequency audible sound can be deviated from the pointing direction of the suction port by making the facing direction of the principal surfaces of the vibrating plate different from the pointing direction of the suction port. Thus, an infant or the like facing the suction port can hardly hear high-frequency audible sound.

Preferably, the discharge port faces to a direction different from a direction in which the suction port is located. According to this structure, high-frequency audible sound leaking from the discharge port cannot be easily heard by infants and the like.

Preferably, the one principal surface or the other principal surface of the vibrating plate faces in a direction in which the discharge port is located. This structure can suppress leakage of high-frequency audible sound from the suction port.

Preferably, the one principal surface and the other principal surface of the vibrating plate face to a direction substantially orthogonal to a direction in which the suction port is located. Thus, since the orientation direction of high-frequency audible sound deviates most from the suction port, it more reliably makes it difficult for the high-frequency audible sound to be heard by infants and the like.

Preferably, the suction device further includes a circuit board that applies a driving voltage to the piezoelectric element, and the one principal surface or the other principal surface of the vibrating plate faces to a direction in which the circuit board is located. Thus, leakage of high-frequency audible sound to the outside can be suppressed by the circuit board, and the circuit board can be effectively cooled by hitting fluid discharged from the discharge plate thereagainst.

Preferably, the suction device further includes a shielding plate, and the one principal surface or the other principal surface of the vibrating plate faces to a direction in which the shielding plate is located. In this case, leakage of high-frequency audible sound to the outside can also be suppressed by the shielding plate.

Preferably, the suction device further includes a housing having a grip portion at a position opposed to the one principal surface and the other principal surface of the vibrating plate. Thus, leakage of high-frequency audible sound to the outside can be suppressed by the hand that grips the housing.

Preferably, a size of the vibrating plate in an in-plane direction of the principal surfaces is larger than a size of an internal space of the housing in a direction in which the one principal surface and the other principal surface of the vibrating plate face. In this case, even when the suction device has a thin structure, the flow of fluid can be produced with high efficiency.

Advantageous Effects of Invention

According to the present disclosure, since high-frequency audible sound caused in the suction device can be hardly heard by infants and the like, a rejection reaction of the infants and the like to an operation of sucking nasal mucus or the like can be suppressed.

BRIEF DESCRIPTION OF THE SEVERAL VIEWS OF THE DRAWINGS

FIGS. 4A, 4B and 4C include schematic views illustrating a vibration manner of the piezoelectric driving unit in the suction device of the first embodiment.

FIG. 5 is a sectional side view of a suction device according to a second embodiment.

DETAILED DESCRIPTION OF THE DISCLOSURE

A plurality of embodiments of the present disclosure will be described below using some specific examples. Each of the embodiments is illustrative and the structures shown in different embodiments can be partially replaced or combined.

Figure 1:
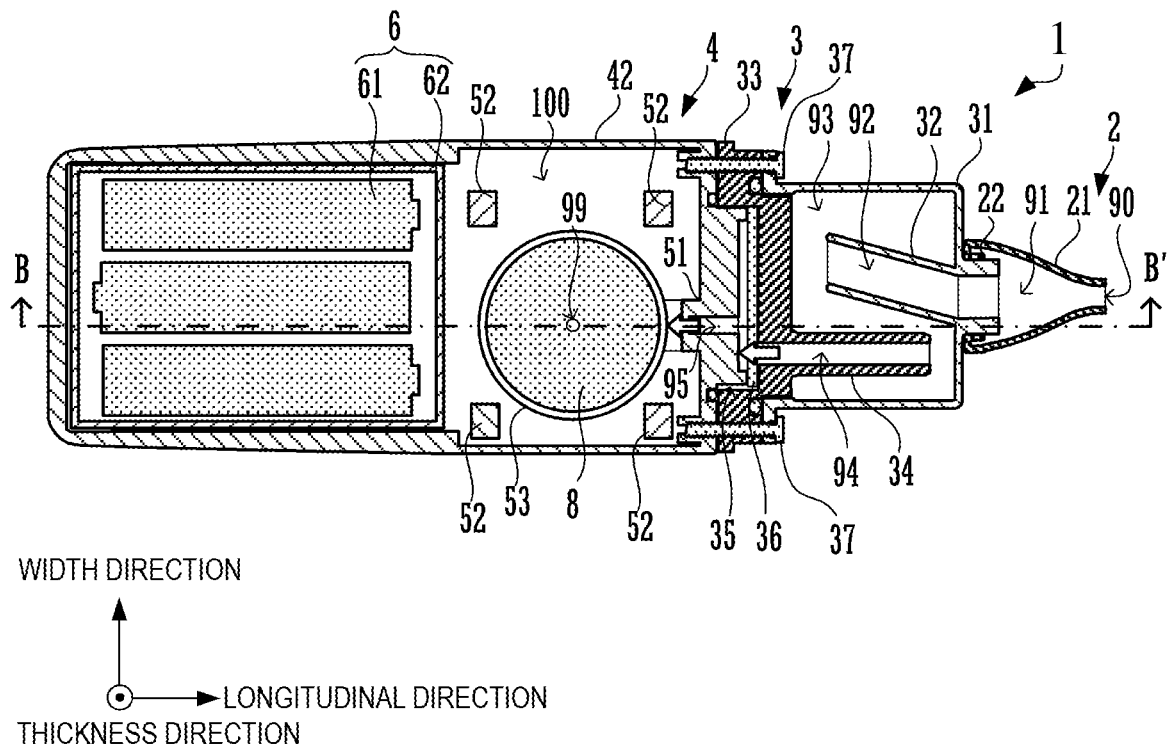
FIG. 1 is a sectional plan view of a suction device according to a first embodiment.
Figure 2:
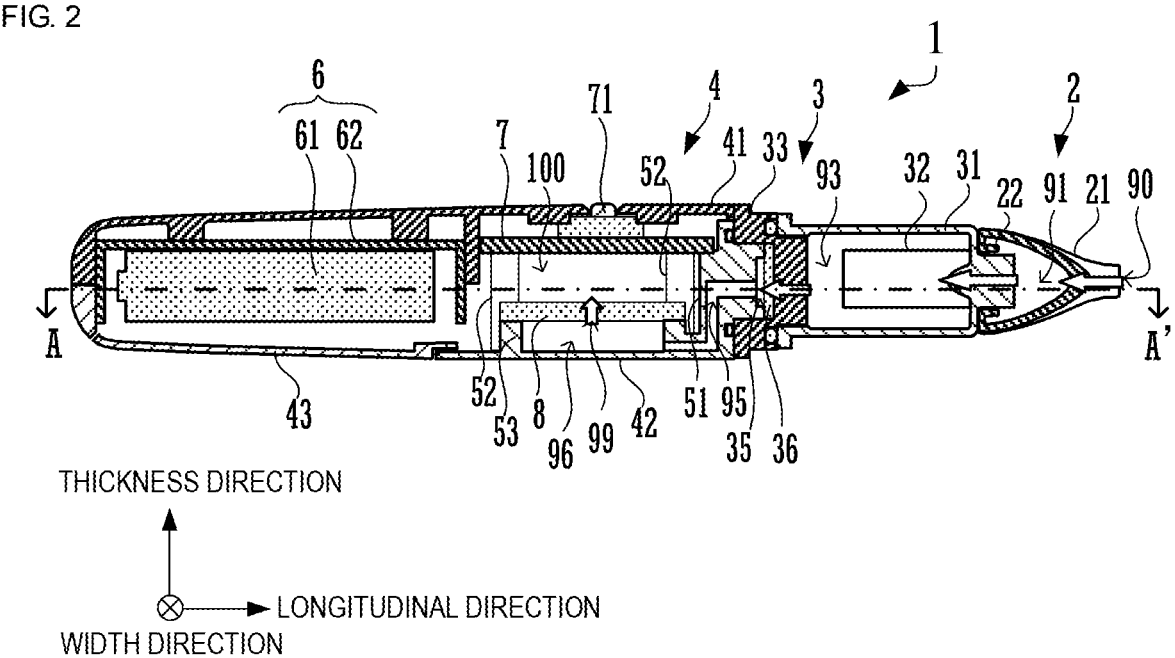
FIG. 2 is a sectional side view of the suction device according to the first embodiment.

FIG. 1 is a sectional side view of a suction device according to a first embodiment, when viewed from a side surface side, and illustrates a cross section taken along one-dot chain line A-A' of FIG. 2. FIG. 2 is a sectional plan view of the suction device of the first embodiment, when viewed from a top side, and illustrates a cross section taken along one-dot chain line B-B' of FIG. 1.

Herein, a suction device 1 illustrated in FIGS. 1 and 2 is a suction device for liquid such as nasal mucus. The suction device 1 is long as a whole to have a longitudinal direction, and is used with one side in the longitudinal direction (hereinafter referred to as a front side) directed toward a patient or the like. The suction device 1 has a width direction and a thickness direction orthogonal to the longitudinal direction, and is thinly structured so that the dimension in the thickness direction is less than the dimension in the width direction.

The suction device 1 is roughly configured as follows. The suction device 1 includes a nozzle 2, a separator 3, and a housing 4. The nozzle 2, the separator 3, and the housing 4 are arranged in this order from the front side toward the rear side in the longitudinal direction. The nozzle 2 is inserted in a nasal cavity of a patient or the like to suck fluid, such as nasal mucus, during use of the suction device 1. The separator 3 separates and stores a mixture, such as nasal mucus, contained in the fluid sucked by the nozzle 2 during use of the suction device 1. The housing 4 is gripped by an operator or the like during use, and sucks the fluid, from which the mixture is removed, from the separator 3.

The suction device 1 also includes a battery unit 6, a circuit board 7, and a piezoelectric driving unit 8 as components built in the housing 4. The battery unit 6 includes batteries 61 and a battery case 62. The battery case 62 holds the batteries 61 replaceably. The circuit board 7 forms a power feeding circuit or the like, and is provided with a power switch 71. The power switch 71 is exposed outside from an opening provided in the housing 4. The circuit board 7 turns on or off power feeding from the battery unit 6 to the piezoelectric driving unit 8 according to the depressed state of the power switch 71. The piezoelectric driving unit 8 generates a negative pressure in a flow passage inside the housing 4 to suck the fluid from the separator 3 into the housing 4.

Detailed structures of the components will be described below.

The nozzle 2 is formed by an integral elastic material, and includes a front end portion 21 and a rear end portion 22. The front end portion 21 is an annular part provided on the front side of the nozzle 2, and the outer shape thereof is inclined to narrow toward the front side. The rear end portion 22 is an annular part provided on the rear side of the nozzle 2, and is turned back toward the inside of the nozzle 2. The nozzle 2 also includes a suction port 90 and a flow passage 91. The suction port 90 is an opening provided at a front end of the nozzle 2 to suck external fluid containing nasal mucus or the like. The flow passage 91 penetrates the inside of the nozzle 2 in the longitudinal direction, and communicates with the suction port 90. The nozzle 2 is connected to the front side of the separator 3 in an airtight state, and is detachable from the separator 3.

The separator 3 includes a case portion 31, a cylindrical portion 32, a cap portion 33, and a cylindrical portion 34. The case portion 31 is a box-shaped member having an opening on the rear side. The cylindrical portion 32 is a cylindrical part attached to the case portion 31, protrudes frontward from a front surface of the case portion 31, and extends rearward from an inner bottom surface of the opening of the case portion 31. The rear end portion 22 of the nozzle 2 is fitted on a front end of the cylindrical portion 32. The cap portion 33 is a lid-shaped member fitted in the rear side of the case portion 31. The cylindrical portion 34 is a cylindrical part attached to the cap portion 33, and extends frontward from the cap portion 33.

The separator 3 also includes flow passages 92, 93, and 94. The flow passage 92 penetrates the inside of the cylindrical portion 32 in the longitudinal direction, and communicates with the flow passage 91 of the nozzle 2. The flow passage 93 is provided inside the case portion 31, and communicates with the flow passage 92 of the cylindrical portion 32. The flow passage 94 penetrates the inside of the cylindrical portion 34 in the longitudinal direction, and communicates with the flow passage 93 of the case portion 31.

The cylindrical portion 32 and the cylindrical portion 34 are arranged in a staggered manner in the longitudinal direction inside the case portion 31, and the flow passage 92 and the flow passage 93 communicate with each other with the flow passage 94 interposed therebetween. Thus, liquid, such as nasal mucus, contained in fluid led from the nozzle 2 to the separator 3 hardly leaks out from the inside (flow passage 93) of the case portion 31, and only gas contained in the fluid is sucked from the separator 3 to the housing 4.

The separator 3 has a recess 35 in a rear surface of the cap portion 33, and is connected to the front side of the housing 4 in an airtight state by fitting the housing 4 in the recess 35. A filter 36 is provided on an inner bottom surface of the recess 35. The filter 36 is a membrane formed of nonwoven paper or sponge, and has the function of preventing liquid, such as nasal mucus, from leaking out from the separator 3 toward the housing 4. The filter 36 does not always need to be provided.

The separator 3 is connected to the housing 4 by screws 37, and can be detached from the housing 4 by removing the screws 37. The case portion 31 and the cap portion 33 can also be detached from each other by removing the screws 37. For this reason, it is possible to remove and clean nasal mucus from the separator 3. O-rings are appropriately provided in connecting portions between the components for airtightness. The components may be detachably connected by using connecting means other than the screws 37, or may be provided integrally.

The housing 4 includes a top-side outer body 41, a bottom-side outer body 42, and a battery cover 43. The top-side outer body 41 is shaped like a thin box having an opening on a bottom side in the thickness direction. The bottom-side outer body 42 is shaped like a thin box having an opening on a top-side in the thickness direction, and is connected to the bottom side of the top-side outer body 41 to form a container. For this reason, an internal space 100 is provided inside the housing 4. In the internal space 100, the battery unit 6, the circuit board 7, and the piezoelectric driving unit 8 are stored. The bottom-side outer body 42 has, on the bottom side, an opening through which the batteries 61 of the battery unit 6 can be replaced, and the battery cover 43 is attached to the bottom side of the bottom-side outer body 42 to cover the opening. The internal space 100 communicates with an external space of the housing 4 with a joint portion between the bottom-side outer body 42 and the battery cover 43 being interposed therebetween, and the pressure in the internal space 100 is substantially equal to outside pressure.

The bottom-side outer body 42 includes a front end portion 51, columnar portions 52, and an annular portion 53. The front end portion 51 is provided at a front end of the bottom-side outer body 42, protrudes toward the separator 3, and is fitted in the recess 35 of the separator 3. The annular portion 53 is a tubular part protruding from an inner bottom surface of the bottom-side outer body 42 toward the top surface in the thickness direction, and supports the piezoelectric driving unit 8 in the internal space 100. The columnar portions 52 are columnar parts protruding from the inner bottom surface of the bottom-side outer body 42 toward the top surface in the thickness direction, and support the circuit board 7 so that the circuit board 7 is opposed to the piezoelectric driving unit 8 with a space therebetween in the internal space 100.

The bottom-side outer body 42 also includes flow passages 95 and 96. The flow passage 95 communicates with the flow passage 94 of the separator 3 and extends rearward inside the front end portion 51 in the longitudinal direction, and a middle portion thereof is bent toward the bottom side in the thickness direction. The flow passage 96 is provided inside the annular portion 53 to be shaped like a bottomed hole, and communicates with the flow passage 95 of the annular portion 53.

The piezoelectric driving unit 8 is shaped like a disc that is thin in the thickness direction, and is joined to a top side of the annular portion 53 to hermetically seal the flow passage 96 inside the annular portion 53. The piezoelectric driving unit 8 has a discharge port 99 that is open near the center of the top surface.

In this suction device 1, when the power switch 71 is turned on and the piezoelectric driving unit 8 is driven, the piezoelectric driving unit 8 sucks fluid from the flow passage 96 on the bottom side, and discharges the fluid from the discharge port 99 into the internal space 100. Thus, the fluid discharged from the discharge port 99 is diffused in the internal space 100, and the fluid pressure falls to the atmospheric pressure. In the flow passage 96 on the bottom side from which the piezoelectric driving unit 8 sucks the fluid, a negative pressure is generated.

Therefore, in the whole suction device 1, the flow of fluid is produced in the flow passage 95 of the housing 4, the flow passages 94, 93, and 92 of the separator 3, and the flow passage 91 of the nozzle 2 by the negative pressure generated in the flow passage 96 of the housing 4, and external fluid is sucked from the suction port 90 of the nozzle 2.

Here, a detailed structure and a vibration manner of the piezoelectric driving unit 8 will be described.

Figure 3:
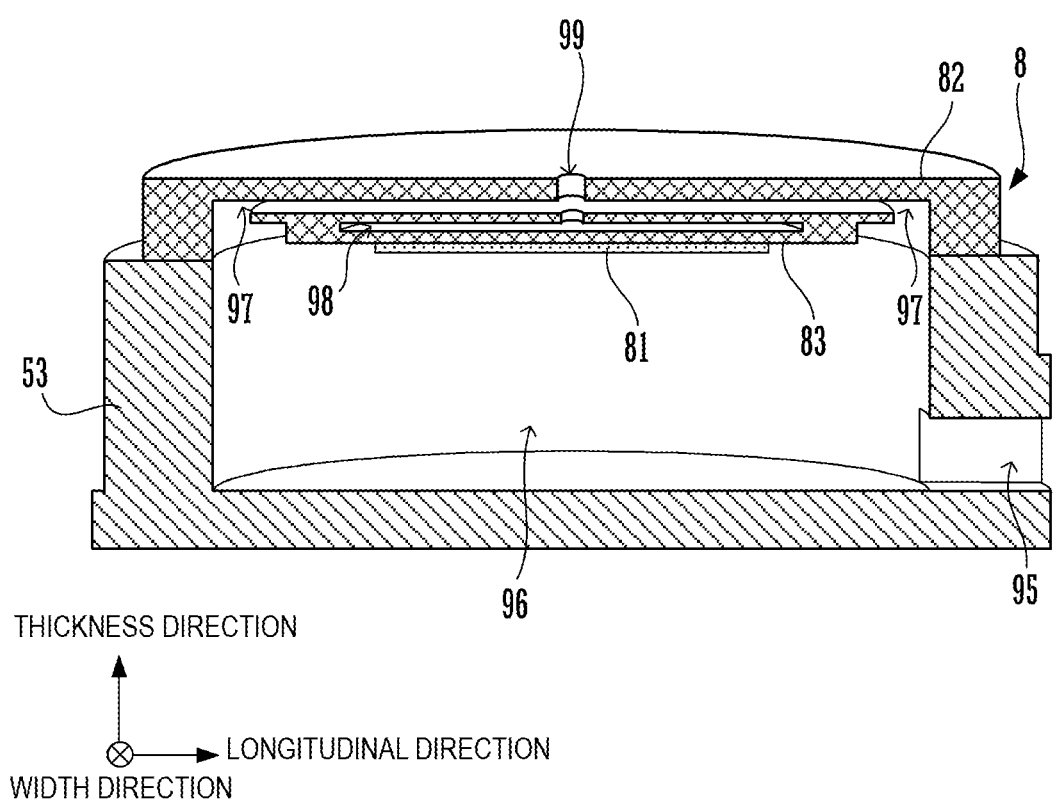
FIG. 3 is an enlarged cross-sectional view of a piezoelectric driving unit in the suction device of the first embodiment.
Figure 6:
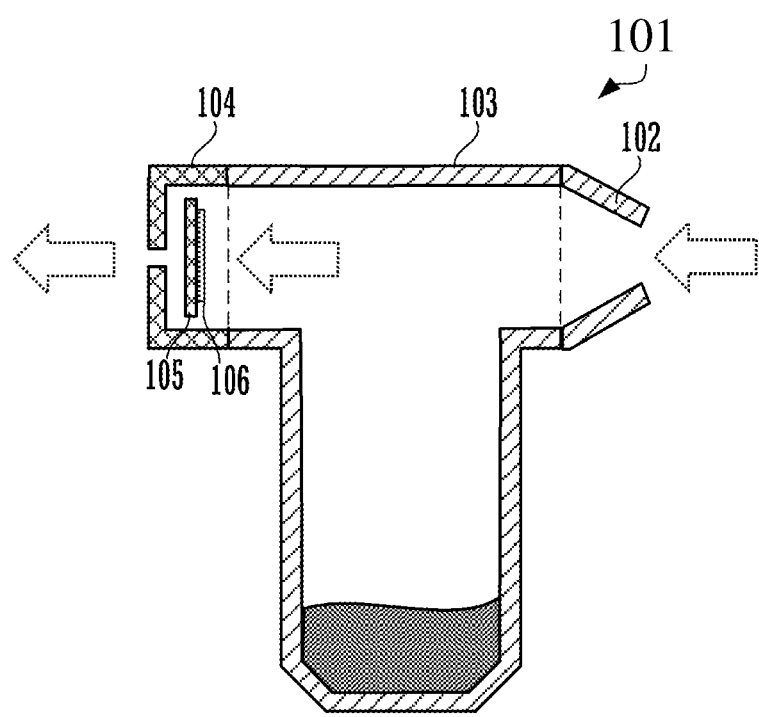
FIG. 6 illustrates a suction device having a conventional structure.

FIG. 3 is an enlarged sectional side view of the surroundings of the piezoelectric driving unit 8. The piezoelectric driving unit 8 includes a piezoelectric element 81 and a structure 82. The outer shape of the structure 82 roughly has a disc shape that is thin in the thickness direction. Inside the structure 82, a flow passage 97 and a pump chamber 98 are provided. Near the center of a top surface of the structure 82, the discharge port 99 is open. The flow passage 97 communicates with the discharge port 99 in the top surface of the structure 82, extends from a portion near the center toward the outer periphery inside the structure 82, and is open in a bottom surface of the structure 82. The flow passage 97 communicates with the flow passage 96 provided on the inner side of the annular portion 53 in the bottom surface of the structure 82. The pump chamber 98 is a thin cylindrical space provided on a bottom side of a communicating portion between the discharge port 99 and the flow passage 97, and is open in the communicating portion between the discharge port 99 and the flow passage 97. The pump chamber 98 forms a part of the flow passage in the suction device 1 together with the flow passage 97.

An inner bottom surface of the pump chamber 98 in the structure 82 is structured as a diaphragm (vibrating plate) 83 capable of bending vibration. The diaphragm 83 is disc-shaped, and has a top surface facing the pump chamber 98 and a bottom surface to which the piezoelectric element 81 is bonded. The top surface of the diaphragm 83 is opposed to the discharge port 99 with the pump chamber 98 interposed therebetween. The piezoelectric element 81 is shaped like a disc that is thin in the thickness direction, and has piezoelectricity to expand and contract in the in-plane direction of the principal surface by the application of an alternating-current driving voltage.

FIGS. 4A, 4B and 4C include schematic views illustrating a vibration manner of the piezoelectric driving unit 8.

The piezoelectric element 81 and the diaphragm 83 are bonded to each other to form a unimorph structure, and are displaced in the thickness direction by driving of the piezoelectric element 81. Specifically, when the piezoelectric element 81 is going to expand from a stationary state illustrated in FIG. 4A, the diaphragm 83 bends convexly toward the piezoelectric element 81 (toward the bottom surface) and the volume of the pump chamber 98 increases, as illustrated in FIG. 4B. Thus, a negative pressure is generated in the pump chamber 98, the negative pressure is transmitted to the flow passage 97 communicating with the pump chamber 98, and the fluid in the flow passage 97 is sucked into the pump chamber 98.

Next, when the piezoelectric element 81 is going to contract, the diaphragm 83 bends convexly toward the pump chamber 98 (toward the top surface), and the volume of the pump chamber 98 decreases, as illustrated in FIG. 4C. Then, since the pump chamber 98 and the discharge port 99 are opposed to each other with the flow passage 97 interposed therebetween, the fluid in the pump chamber 98 is discharged from the discharge port 99 to the outside (internal space 100), and the fluid in the flow passage 97 is drawn by the flow of the above fluid and is discharged from the discharge port 99.

In this way, in the piezoelectric driving unit 8, periodic volume fluctuation and pressure fluctuation are repeated in the pump chamber 98 along with bending vibration of the piezoelectric element 81 and the diaphragm 83, and inertial force acts on the flow of gas. Thus, the gas flow to discharge the fluid in the flow passage 97 from the discharge port 99 is steadily produced.

In the piezoelectric driving unit 8, since the members do not friction (slide) with each other, the produced driving sound and vibration are smaller than in the conventional electric motor driving unit. Therefore, the driving sound and vibration of the piezoelectric driving unit 8 leaking out from the suction device 1 to the external space are extremely small. Further, since the diaphragm 83 is provided opposed to the discharge port 99 with the flow passage 97 and the pump chamber 98 interposed therebetween, fluid efficiency of the piezoelectric driving unit 8 is high, and the suction device 1 can easily suck even a high-viscosity fluid such as nasal mucus.

However, there is a need to apply a driving voltage of a relatively high frequency of about 1000 Hz to the piezoelectric driving unit 8. For this reason, the vibration frequency of the diaphragm 83 is also a relatively high frequency of about 1000 Hz. Thus, audible sound in a frequency band that nearly coincides with the vibration frequency (high-frequency audible sound) is produced from the diaphragm 83 and the discharge port 99. Since such high-frequency audible sound has directivity in the vibrating direction of the diaphragm 83 (direction in which the principal surfaces face) and in the opening direction of the discharge port 99, it tends to be loud in its orientation direction and not to be loud in directions deviating from its orientation direction.

Accordingly, in the suction device 1, the piezoelectric driving unit 8 is disposed so that the vibrating direction of the diaphragm 83 and the pointing direction of the discharge port 99 coincide with the thickness direction of the suction device 1 substantially orthogonal to the direction in which the suction port 90 is located. Thus, the orientation direction of high-frequency audible sound produced in the piezoelectric driving unit 8 coincides with the thickness direction of the suction device 1, and the nozzle 2 at the front end of the suction device 1 in the longitudinal direction is located out of the orientation direction of the high-frequency audible sound. Further, the pointing direction of the nozzle 2 is made different from the orientation direction of the high-frequency audible sound. Still further, the piezoelectric driving unit 8 is configured so that the diaphragm 83 and the discharge port 99 are opposed to each other. The diaphragm 83 and the discharge port 99 are disposed physically far from the nozzle 2 and the suction port 90 so that high-frequency audible sound produced in the piezoelectric driving unit 8 is hardly transmitted thereto. From these, high-frequency audible sound can be hardly heard by infants and the like subjected to the suction operation of inserting the nozzle 2 into the nasal cavity.

Since the exterior of the housing 4 is structured to be gripped by the operator's hand, the operator's hand that covers the portion opposed to the piezoelectric driving unit 8 can block high-frequency audible sound leaking out from the housing 4. Further, since the circuit board 7 is disposed as opposed to the discharge port 99 of the piezoelectric driving unit 8 inside the housing 4, it can block high-frequency audible sound leaking toward the discharge port 99 of the piezoelectric driving unit 8. From these, high-frequency audible sound can also hardly leak out of the housing 4. Moreover, the fluid discharged from the discharge port 99 hits the circuit board 7, and this can increase the effect of cooling the circuit board 7.

As described above, according to the suction device 1 of this embodiment, high-frequency audible sound produced in the piezoelectric driving unit 8 can be hardly heard by infants and the like subjected to the operation of sucking nasal mucus, and the rejection reaction of the infants and the like to the suction operation can be suppressed. Further, in the suction device 1, the piezoelectric driving unit 8 is disposed in a lying state inside the housing 4 so that both principal surfaces of the piezoelectric driving unit 8 face in the thickness direction of the suction device 1. Hence, the size of the piezoelectric driving unit 8 in the direction of the principal surfaces can be made larger than the size in the thickness direction in the internal space 100 of the housing 4. Therefore, even when the suction device 1 has a thin structure, the flow of fluid can be efficiently produced using the large-sized piezoelectric driving unit 8.

Next, a suction device according to a second embodiment of the present disclosure will be described.

FIG. 5 is a sectional side view of the suction device according to the second embodiment.

While a suction device 1A illustrated in FIG. 5 has almost the same configuration as that of the above-described first embodiment, a housing 4 includes a shielding plate 8A. The shielding plate 8A is disposed on a top side of a piezoelectric driving unit 8 in an internal space 100 of the housing 4 to be at a distance from the piezoelectric driving unit 8. Between the shielding plate 8A and the piezoelectric driving unit 8, not less than a fixed distance is provided so that discharging of fluid from the piezoelectric driving unit 8 is not hindered. By providing this shielding plate 8A, high-frequency audible sound leaking toward a discharge port 99 of the piezoelectric driving unit 8 can be blocked, and high-frequency audible sound can be even less easily heard outside the housing 4.

The present disclosure can be carried out as in the above-described embodiments. The shape of the nozzle 2 is not limited to the above example and may be other shapes. For example, when the suction device 1 is used as a breast-milk suction device or a phlegm suction device, the nozzle 2 may be shaped like a funnel or a straw.

The structure for separating gas and a mixture (liquid) contained in fluid in the separator 3 may be different from the above-described one. For example, the gas and the liquid contained in the fluid can also be easily separated by adopting a valve structure in the separator 3.

The structure of the piezoelectric driving unit 8 may be different from the above-described one. For example, the number of discharge-side flow passages and the number of suction-side flow passages provided in the piezoelectric driving unit 8 and the paths thereof can be changed appropriately.

The fluid to be sucked is not limited to liquid, and may be a solid or gel substance. The present disclosure is also applicable to, for example, a dust collection device for collecting minute dust and powder dust and a device for collecting extra glue or adhesive applied to a workpiece.

1 suction device
  2 nozzle
  3 separator
  4 housing
  6 battery unit
  7 circuit board
  8 piezoelectric driving unit
  21 front end portion
  22 rear end portion 31 case portion
32 cylindrical portion
33 cap portion
34 cylindrical portion
35 recess
36 filter
41 top-side outer body
42 bottom-side outer body
43 battery cover
51 front end portion
52 columnar portion
53 annular portion
61 battery
62 battery case
71 power switch
81 piezoelectric element
82 structure
83 diaphragm (vibrating plate)
90 suction port
91, 92, 93, 94, 95, 96, 97 flow passage
98 pump chamber (flow passage)
99 discharge port
100 internal space

The invention claimed is:
1. A hand-held suction device having:
a housing having a grip portion on an outer surface of the housing, the housing having an elongated shape with a major longitudinal axis and minor lateral axes that are orthogonal to the major longitudinal axis, the grip portion extending in a longitudinal direction of the housing,
a suction port providing fluid communication between an outside and an inside of the housing, the suction port disposed on a distal end of the housing for drawing fluid into the housing,
a flow passage located in the housing and communicating with the suction port, and
a piezoelectric driving unit comprising:
a plate-like structure having a discharge port located in the housing and communicating with the flow passage,
a top plate having an opening facing the discharge port,
a vibrating plate facing the opening and the discharge port, a pump chamber located along a part of the flow passage in the housing, the pump chamber formed by the top plate and the vibrating plate, and communicating with the flow passage at the opening, and
a piezoelectric element attached to one principal surface of the vibrating plate to displace the vibrating plate, wherein a negative pressure is generated in the pump chamber to suck fluid from the opening by increasing a volume of the pump chamber, and the fluid sucked from the opening is discharged through the opening and the discharge port by reducing the volume of the pump chamber,
wherein a space between the top plate and the plate-like structure is a part of the flow passage,
wherein discharging fluid through the discharge port causes fluid to flow from the suction port to the discharge port,
wherein a direction of movement of the one principal surface and another principal surface of the vibrating plate is not aligned with a longitudinal axis of the suction port, and
wherein the grip portion is located on a portion of the housing opposed to the piezoelectric driving unit.

2. The hand-held suction device according to claim 1, wherein a longitudinal axis of the discharge port is not aligned with the longitudinal axis of the suction port.

3. The hand-held suction device according to claim 1, wherein the direction of movement of the one principal surface or the another principal surface of the vibrating plate is not aligned with a longitudinal axis of the discharge port.

4. The hand-held suction device according to claim 1, wherein the direction of movement of the one principal surface and the another principal surface of the vibrating plate is substantially orthogonal to the longitudinal axis of the suction port.

5. The hand-held suction device according to claim 1, further comprising:
a circuit board applying a driving voltage to the piezoelectric element,
wherein the one principal surface or the another principal surface of the vibrating plate faces in a direction in which the circuit board is located.

6. The hand-held suction device according to claim 1, further comprising a shielding plate, wherein the one principal surface or the another principal surface of the vibrating plate faces in a direction in which the shielding plate is located.

7. The hand-held suction device according to claim 1, wherein the grip portion is at a position opposed to the one principal surface and the another principal surface of the vibrating plate.

8. The hand-held suction device according to claim 7, wherein a size of the vibrating plate in an in-plane direction of the principal surfaces is larger than a size of an internal space of the housing in a direction in which the one principal surface and the another principal surface of the vibrating plate face.

9. The hand-held suction device according to claim 2, wherein the direction of movement of the one principal surface or the another principal surface of the vibrating plate aligns with the longitudinal axis of the discharge port.

10. The hand-held suction device according to claim 2, wherein the direction of movement of the one principal surface and the another principal surface of the vibrating plate is substantially orthogonal to the longitudinal axis of the suction port.

11. The hand-held suction device according to claim 3, wherein the direction of movement of the one principal surface and the another principal surface of the vibrating plate is substantially orthogonal to the longitudinal axis of the suction port.

12. The hand-held suction device according to claim 2, further comprising:
a circuit board applying a driving voltage to the piezoelectric element,
wherein the one principal surface or the another principal surface of the vibrating plate faces in a direction in which the circuit board is located.

13. The hand-held suction device according to claim 3, further comprising:
a circuit board applying a driving voltage to the piezoelectric element,
wherein the one principal surface or the another principal surface of the vibrating plate faces in a direction in which the circuit board is located.

14. The hand-held suction device according to claim 4, further comprising:
a circuit board applying a driving voltage to the piezoelectric element, wherein the one principal surface or the another principal surface of the vibrating plate faces in a direction in which the circuit board is located.

15. The hand-held suction device according to claim 2, further comprising a shielding plate, wherein the one principal surface or the another principal surface of the vibrating plate faces in a direction in which the shielding plate is located.

16. The hand-held suction device according to claim 3, further comprising a shielding plate, wherein the one principal surface or the another principal surface of the vibrating plate faces in a direction in which the shielding plate is located.

17. The hand-held suction device according to claim 4, further comprising a shielding plate, wherein the one principal surface or the another principal surface of the vibrating plate faces in a direction in which the shielding plate is located.

18. The hand-held suction device according to claim 5, further comprising a shielding plate, wherein the one principal surface or the another principal surface of the vibrating plate faces in a direction in which the shielding plate is located.

19. The hand-held suction device according to claim 2, wherein the grip portion is at a position opposed to the one principal surface and the another principal surface of the vibrating plate.

20. The hand-held suction device according to claim 3, wherein the grip portion is at a position opposed to the one principal surface and the another principal surface of the vibrating plate.

* * * * *